United States Patent
Jenkins

(10) Patent No.: US 7,280,864 B2
(45) Date of Patent: Oct. 9, 2007

(54) METHOD AND APPARATUS FOR AUTOMATED SELECTION OF CORRECT IMAGE FOR QUANTITATIVE ANALYSIS

(75) Inventor: John H Jenkins, Grand Prairie, TX (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 803 days.

(21) Appl. No.: 10/065,893

(22) Filed: Nov. 27, 2002

(65) Prior Publication Data

US 2004/0102693 A1    May 27, 2004

(51) Int. Cl.
*A61B 5/05* (2006.01)

(52) U.S. Cl. ............. 600/428; 600/509; 600/413; 378/8

(58) Field of Classification Search ........ 600/407–410, 600/428, 509, 413; 382/128; 378/8
See application file for complete search history.

(56) References Cited

U.S. PATENT DOCUMENTS 6,351,547 B1    2/2002    Johnson et al.
6,501,979 B1    12/2002   Manning et al.

OTHER PUBLICATIONS

"The Development of an Application Profile for DICOM Waveforms in the Cathlab" T. Becker et al., Computer in Cardiology, 1999, pp. 97-99.

"A Digital Image Archive Solution for Multiple Modalities in a Cardiological Department" T. Becker et al., Computers in Cardiology, 1999, pp. 367-369.

"ECG-Based Selection of Angiographic Images using DICOM Facilities" J. Christiaens et al., Computers in Cardiology, 1999, pp. 447-450.

*Primary Examiner*—Brian L. Casler
*Assistant Examiner*—John F. Ramirez
(74) *Attorney, Agent, or Firm*—Ostrager Chong Flaherty & Broitman P.C.

(57) ABSTRACT

A method for selecting images for coronary analysis using time stamps to correlate cardiovascular images to corresponding physiological or hemodynamic monitoring, e.g., ECG, data. The method uses time stamps that are intrinsic to a distributed network clock synchronization protocol for correlation of images and data. A coronary analysis system is employed to correlate images with physiologic data, e.g., using time stamp data as well as offset data derived using the distributed network clock synchronization protocol.

22 Claims, 5 Drawing Sheets

| FIG.2A |
| FIG.2B |

US 7,280,864 B2

METHOD AND APPARATUS FOR AUTOMATED SELECTION OF CORRECT IMAGE FOR QUANTITATIVE ANALYSIS

BACKGROUND OF INVENTION

This invention generally relates generally to diagnostic medical imaging and to methods and systems for storing cardiac images and ECG waveforms. More particularly, the invention relates to methods and systems for selecting images for heart analysis based on ECG waveform characteristics, thereby allowing more efficient diagnosis by the trained professional.

A coronary angiogram (or arteriogram) is an x-ray of the arteries located on the surface of the heart (the coronary arteries). Such images help the physician to see if any artery is blocked, usually by fatty plaque. If the artery is blocked, the patient may be diagnosed with coronary artery disease ("CAD").

A coronary angiogram is often acquired along with other catheter-based tests as part of a procedure called cardiac catheterization, which includes measurement of blood pressure, taking samples for blood tests, a coronary angiogram and a left ventriculogram. In order to take an angiogram, the physician needs to inject a special dye (contrast medium) into the coronary arteries. To do this, the physician inserts a thin tube (catheter) through a blood vessel, usually in the femoral artery (groin/upper thigh area), arm or wrist, all the way up through to the heart. Once the catheter is in place, the physician can inject the dye through the catheter and into the coronary arteries. Then the x-ray can be taken.

Depending on what the angiogram shows, the physician may recommend treatments such as medication, a catheter-based procedure (e.g., a balloon angioplasty or coronary stenting) or surgery (e.g., bypass surgery). A coronary angiogram (or arteriogram) is one of the most accurate tests in the diagnosis of CAD, and over a million coronary angiograms are taken each year. The angiogram is used to pinpoint the location and severity of CAD. For example, it could reveal blockage in an artery due to either a build-up of plaque or abnormalities in the wall of the heart.

The above-described cardiac angiography is typically performed in a surgical imaging area called a cardiac catheterization laboratory. The images are acquired using cardiovascular x-ray imaging equipment The resulting images are stored and viewed on film or, increasingly, kept in digital form as DICOM (Digital Imaging and Communications in Medicine) images and stored and viewed electronically. These digital images are available for review and analysis at a physician review workstation.

During catheterization procedures, the patient also undergoes physiological monitoring using a hemodynamic monitoring system. The hemodynamic monitoring system hooks up to a patient via externally placed leads that monitor the electrical impulses from the heart and records the heart's electrical activity in the form of a waveform. This record, called an electrocardiogram (ECG), is analyzed by well-known software that measures the heart's rhythms and electrical impulses, allowing the physician to detect heart irregularities, disease and damage. The ECG data, including waveforms and results of analysis, is typically stored in a computer database.

Quantitative image analysis refers to methods of measuring angiographic images. Typically, these images are dynamic, needing to be "filmed" as the radiographic opaque dye is injected, and are reviewed for diagnosis in moving picture format. Quantitative image analysis is largely a manual process. The cardiologist will normally search through a serial run of angiographic images and move the images backward and forward until the cardiologist is satisfied that he/she has found an image representing what the cardiologist is seeking (e.g., the systolic or diastolic images). This takes valuable time that could be used in treating the patient.

Once the correct angiographic image has been selected, quantitative image analysis can be performed. A well-known analysis technique is left ventricular analysis (wall motion, ejection fraction and volume). A left ventricular analysis is carried out as follows. Dye is injected into the left ventricle at the same time the imaging system is activated. Typically, the resulting images are captured in a digital format and redisplayed through the imaging equipment. The user selects the largest (diastole) frame and the smallest (systole) frame and uses an analytical process (software) to compare the two traces. The outcome is an ejection fraction or a value that reflects the patient's heart pumping capability and may include a calculation of the actual volume pumped with each beat.

There is a need for a system that facilitates automated selection of the correct image or images for quantitative image analysis. For example, quantitative coronary analysis typically requires selection of a stored frame of imaging data acquired from a patient concurrent with a predetermined event in the patient's cardiac cycle, the latter being indicated by a feature or characteristic on a stored ECG waveform of the patient. However, synchronization of imaging data and physiologic data, both retrieved from storage, for a given study is problematic and time consuming. More specifically, the respective time stamps on the imaging and physiologic data must be synchronized. An automated frame selection technique that takes into account the need for network time synchronization is desirable.

SUMMARY OF INVENTION

The invention is directed in part to a method for selecting images for coronary analysis using time stamps to correlate cardiovascular images to corresponding physiological or hemodynamic monitoring, e.g., ECG, data. The method uses time stamps as well as the offsets that are intrinsic to a distributed network clock synchronization protocol for correlation of images and data. The invention is also directed in part to a coronary analysis system that correlates images with physiologic data, e.g., using time stamp data as well as offset data derived using the distributed network clock synchronization protocol.

One aspect of the invention is a method for synchronizing frames of imaging data with physiologic data, comprising the following steps: (a) acquiring frames of imaging data representing a succession of images of a patient's heart during a study using an imaging system; (b) automatically time stamping each acquired frame with respective times generated by a first clock; (c) automatically determining respective offsets of the first clock relative to a reference clock for each time stamp associated with the acquired frames; (d) storing the acquired frames and the time stamps and the offsets associated with the acquired frames; (e) acquiring physiologic data from the patient during the study using a hemodynamic monitoring system; (f) automatically time stamping data in the acquired physiologic data representing one or more predetermined cardiac events with respective times generated by a second clock; (g) automatically determining respective offsets of the second clock relative to the reference clock for each time stamp associated with the physiologic data; and (h) storing the acquired physiologic data and the time stamps and the offsets associated with the acquired physiologic data.

Another aspect of the invention is a cardiology analysis system comprising an operator interface, a display monitor and a computer programmed to perform the following steps: compensating for a lack of synchronism between a first clock used to time stamp a plurality of acquired frames of imaging data and a second clock used to time stamp acquired physiologic data representing predetermined cardiac events; and selecting one of the frames that was acquired at a time substantially the same as the time when a predetermined cardiac event occurred based on the results of the compensating step.

A further aspect of the invention is a system comprising: an imaging system programmed to time stamp acquired frames of imaging data based on time measured by a first local clock; a hemodynamic monitoring system programmed to time stamp acquired physiologic data corresponding to predetermined cardiac events based on time measured by a second local clock; and a computer programmed to communicate reference clock time to the imaging system and to the hemodynamic monitoring system in accordance with a network time synchronization protocol. The imaging system and the hemodynamic monitoring system are each further programmed to perform the following steps: (a) calculating a respective link delay; (b) calculating a respective local offset; and (c) associating each of the local offsets with a respective time stamp.

Yet another aspect of the invention is a system comprising: an imaging system programmed to time stamp acquired frames of imaging data based on time measured by a first local clock; a hemodynamic monitoring system programmed to time stamp acquired physiologic data corresponding to predetermined cardiac events based on time measured by a second local clock; and a computer programmed to communicate reference clock time to the imaging system and to the hemodynamic monitoring system in accordance with a network time synchronization protocol. The imaging system and the hemodynamic monitoring system are each further programmed to perform the following steps: (a) calculating a respective link delay; (b) calculating a respective local offset; and (c) adjusting a respective one of the first and second local clocks to match the reference clock. The time stamps of the imaging system and the hemodynamic monitoring system are respectively derived from the adjusted first and second local clocks.

A further aspect of the invention is a method for synchronizing a frame of imaging data with a physiologic datum, comprising the following steps: (a) automatically determining a first offset of a first local clock relative to a reference clock, the first local clock dictating the time of day in an imaging system; (b) automatically adjusting the first local clock by an amount that is a function of the first offset to synchronize the first local clock with the reference clock; (c) automatically determining a second offset of a second local clock relative to the reference clock, the second local clock dictating the time of day in an hemodynamic monitoring system; (d) automatically adjusting the second local clock by an amount that is a function of the second offset to synchronize the second local clock with the reference clock; (e) acquiring a frame of imaging data representing an image of a patient's heart during a study using the imaging system; (f) automatically time stamping the acquired frame with a time generated by the adjusted first local clock; (g) storing the acquired frame and the time stamp associated with the acquired frame as an imaging file; (h) acquiring physiologic data from the patient during the study using the hemodynamic monitoring system; (i) automatically time stamping a datum in the acquired physiologic data representing a predetermined cardiac event with a time generated by the adjusted second local clock; and (j) storing the acquired physiologic data and the time stamp associated with the acquired physiologic data as a physiology file.

Other aspects of the invention are disclosed and claimed below.

BRIEF DESCRIPTION OF DRAWINGS

Reference will now be made to the drawings in which similar elements in different drawings bear the same reference numerals.

DETAILED DESCRIPTION

Figure 1:
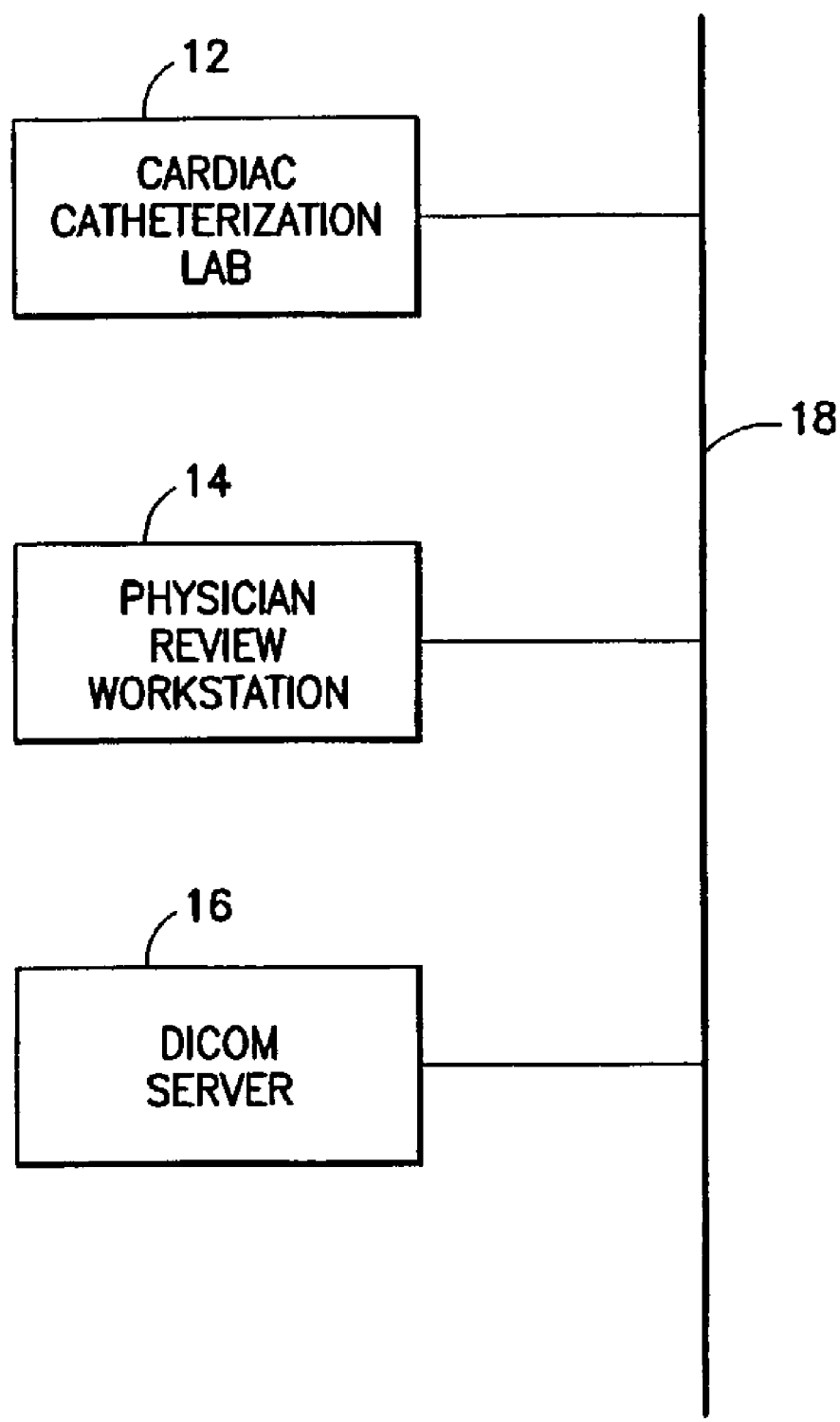
FIG. 1 is a block diagram depicting a network for facilitating storage and review of data acquired in a cardiac catheterization laboratory in a hospital or other health service facility.

FIG. 1 depicts a local area network (LAN) 18 that facilitates communication between a cardiac catheterization laboratory 12 (or rather systems housed in the laboratory), a physician review or overview workstation 14 and a DICOM server 16. For example, angiographic x-ray images acquired by imaging equipment at the catheterization lab 12 and formatted as DICOM objects can be stored in a database (not shown) accessed via the DICOM server 16. Thereafter, a physician at the workstation 14 can retrieved those stored images from the DICOM server 16 and view them on the display monitor of the workstation. The computer at the workstation may be programmed to enable the physician to perform quantitative image analysis on the retrieved images. However, as described in the Background of the Invention section, certain analysis, such as left ventricular analysis, require that the images corresponding to particular cardiac events (e.g., diastole and systole) be correctly selected by the physician. The physician will normally search through the serial run of images of a particular study, scanning forward and backward until the physician is satisfied that the displayed image corresponds to the desired cardiac event.

Figures 2, 2A:
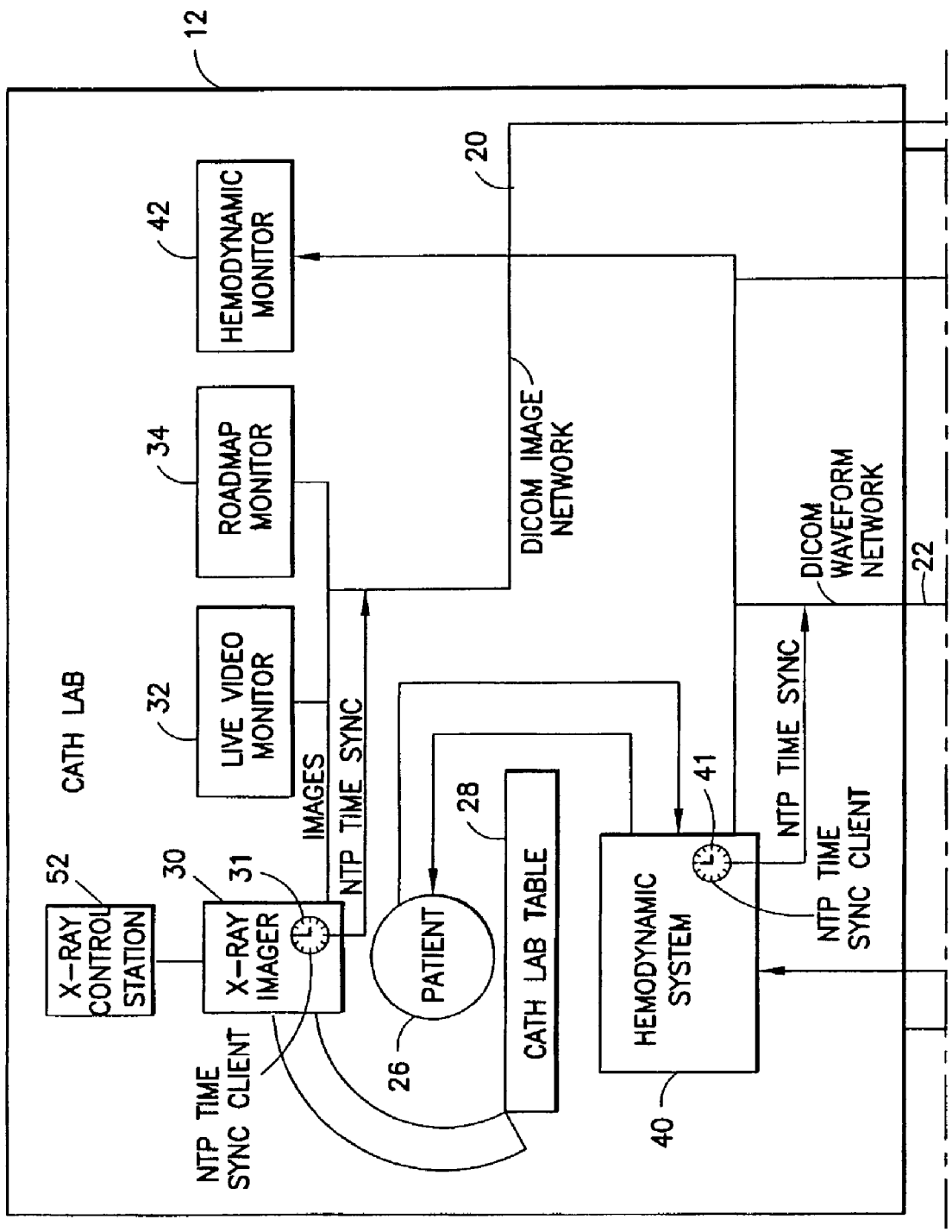
FIGS. 2A and 2B, when viewed in conjunction, constitute FIG. 2, which is a block diagram depicting a cardiac catheterization laboratory networked to an asynchronous DICOM server with NTP time synchronization server in accordance with one embodiment of the invention.
Figure 2B:
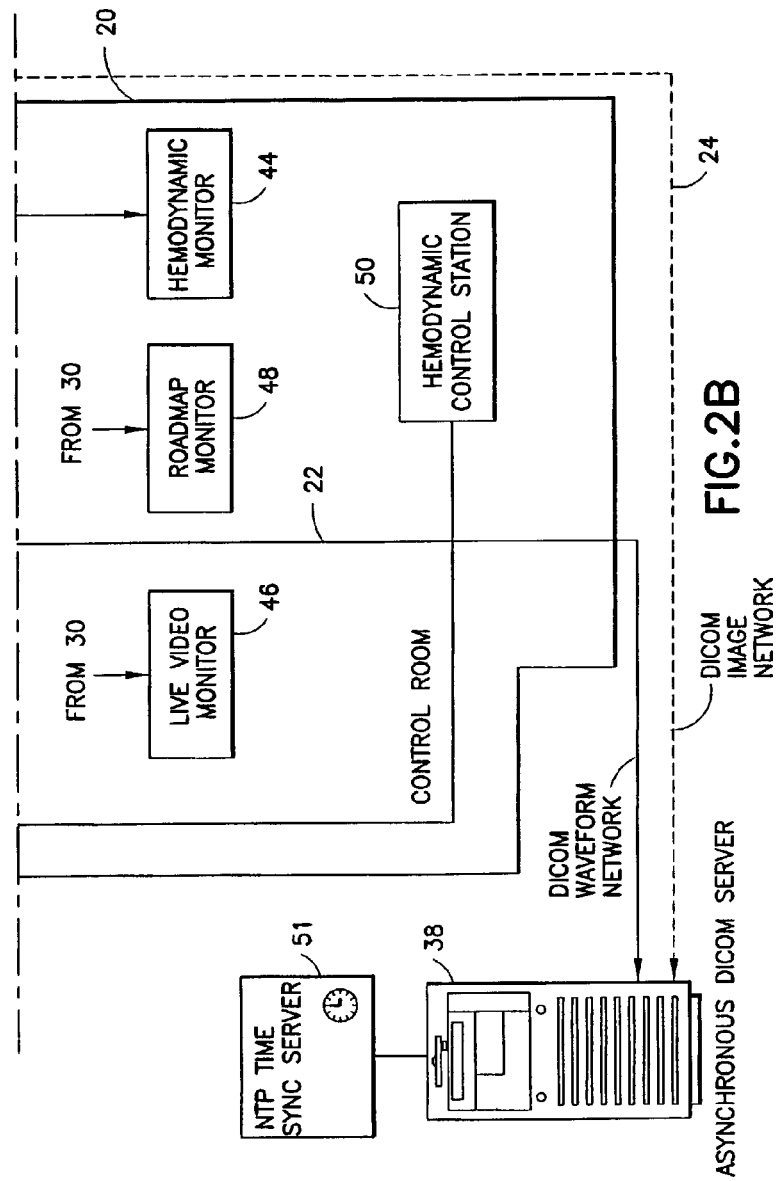

FIGS. 2A and 2B are block diagrams depicting a networked system in accordance with one embodiment of the present invention. These drawings need to be viewed in conjunction as shown in FIG. 2. In FIG. 2A, the area demarcated by the rectangular boundary represents a cardiac catheterization laboratory 12. The adjoining area demarcated by the six-sided polygon (formed when FIGS. 2A and 2B are conjoined) represents a control room 20. An asynchronous DICOM server 38 programmed with NTP time synchronization server software 51 and database management software (not indicated) is shown located outside the catheterization laboratory 12 and outside the control, but may be located inside either room. The DICOM server 38 manages a database not shown, which database, as explained in detail below, contains imaging and physiologic data stored as DICOM objects.

Inside the catheterization laboratory 12, cardiac catheterization can be performed on a patient 26 placed on a special examination table 28. The procedure involves the placement of a catheter (hollow tube) into the patient's heart in order to evaluate the anatomy and function of the heart and surrounding blood vessels. After local anesthesia is given, a catheter is inserted into blood vessels in the groin, arm or neck. The catheter is advanced through the vessels to the heart. Once in the heart, the catheter can be maneuvered to various locations within the heart. By attaching the catheter to a pressure transducer, the pressures within different chambers can be measured. Blood samples can also be withdrawn from different locations. In addition, dye is injected through the catheter while a series of rapid x-ray images are recorded by an x-ray imager 30. The x-ray imager 30 is controlled by a technician located at an x-ray control station 52. The x-ray images can be viewed in video format on live video monitors 32 and 46 respectively located in the catheterization laboratory 12 and control room 20. This video shows the blood flowing through the heart chambers or through the blood vessels connected to the heart. This procedure is known as angiography. An angiogram helps to provide a roadmap of the blood vessels. The contrast-enhanced roadmap image is displayed on roadmap monitors 34 and 48, respectively located in the catheterization laboratory 12 and control room 20, and aids in catheter guidance.

Each frame of imaging data acquired by the x-ray imager 30 is time stamped with the local time with reference to a first local clock 31 located in or connected to the x-ray imager 30. Each frame is later encapsulated in a DICOM object, with the associated time stamp for that frame being inserted in a predetermined field in a header in the DICOM object. The DICOM object can then be uploaded to the DICOM server 38 (shown in FIG. 2B) via a DICOM image network 20. The DICOM server 38 is programmed with database management software for managing a DICOM image database (not shown). This database may reside on the DICOM server 38 or on a separate computer connected to the DICOM server 38. The DICOM objects from the x-ray imager 30 are stored in the database.

The cardiac catheterization laboratory 12 also houses a hemodynamic monitoring system, such as the MacLab 7000 system manufactured and sold by GE Medical Systems. This system is manned by a technician, who is seated at a hemodynamic control station 50 located in the control room 20. During catheterization procedures, the patient undergoes physiological monitoring. The hemodynamic monitoring system 40 records physiologic data, including ECG waveforms acquired from electrodes placed on the patient. The data acquired by the hemodynamic monitoring system is displayed on hemodynamic monitors 42 and 44 respectively located in the catheterization laboratory 12 and the control room 20. The hemodynamic monitoring system 40 is also programmed to perform ECG analysis, producing signals, i.e., pointers, that indicate features of the ECG waveform, such as the exact diastolic and systolic heart beats. The hemodynamic monitoring system can also automatically acquire and display 12-lead ECGs, continuous ST segment analysis, respiration rate, thermodilution cardiac output, $SpO_2$ level, noninvasive blood pressure and up to four invasive pressures.

Furthermore, the hemodynamic monitoring system 40 maintains a "cath lab event log", in which the various procedures being performed are recorded. The hemodynamic technician controls all information in the cath lab event log. The technician has his/her hands free and is watching/listening to the entire cath lab procedure behind leaded glass. The technician knows the projection being imaged and the arterial branch selected for recording. This information can be entered into the event log before the injection of dye.

The aforementioned pointers, indicating characteristic features of the acquired EGG waveforms and corresponding to well-known cardiac events, (such as diastole and systole), are time stamped by the hemodynamic monitoring system 40. These pointers are time stamped with the local time with reference to a second local clock 41 located in or connected to the hemodynamic monitoring system 40. The time-stamped EGG waveforms are later encapsulated in DICOM objects, with the associated time stamps being inserted in predetermined fields in a header in each DICOM object. These DICOM objects are uploaded to the DICOM server 38 via a DICOM waveform network 22.

It is customary to perform quantitative imaging analysis on the acquired x-ray images. The software modules for quantitative analysis may be resident on the x-ray control station 52, on the hemodynamic control station 50 or on any physician review workstation (such as station 14 depicted in FIG. 1) capable of communicating with the DICOM server 38, where the acquired data for all studies are stored. Such quantitative analysis requires the selection of images that were acquired substantially in synchronization with certain cardiac events of interest. The goal is to automate this frame selection process. In order to select the frame of imaging data in synchronism with a particular cardiac event, one could look at the time-stamped pointer corresponding to that particular cardiac event and then find the frame of imaging data having a time stamp that is closest in time. However, this procedure does not take into account the circumstance that the respective local clocks for the two data acquisition systems, namely, x-ray imager 30 and hemodynamic monitoring system 40, may not be synchronized, i.e., the respective times of the two clocks are different by an amount that will be referred to herein as an "offset". Moreover, the magnitude of the offset between the two local clocks can change over time.

One embodiment of the invention compensates for out-of-sync local clocks by providing NTP time synchronization server software module 51 that resides in the DICOM server 38 and also by providing the two data acquisition systems 30 and 40 with respective NTP time synchronization client software modules. Each NTP time synchronization client software module communicates with the NTP time synchronization server software module 51 in accordance with a network time protocol for the purposes of independently synchronizing the respective local clocks 31 and 41 of the data acquisition systems 30 and 40 to a reference clock associated with module 51. Each NTP time synchronization client software module initiates a time request exchange with the NTP time synchronization server software module 51. As a result of this exchange, the client is able to calculate the link delay, its local offset, and adjust its local clock to match the reference clock at the computer (i.e., DICOM server 38) where the server software module 51 resides. Once the local clocks have been synchronized with the reference clock, the client updates its local clock periodically, e.g., once every minute.

In accordance with this embodiment of the invention, frames of imaging data acquired by the x-ray imager 30 can be synchronized with features in the physiologic data acquired by the hemodynamic monitoring system that represent predetermined cardiac events of interest. The procedure is as follows.

Frames of imaging data representing a succession of images of a patient's heart during a study are acquired using the imager 30. The imager 30 is programmed to automatically time stamp each acquired frame with respective times generated by the local clock that dictates the time of day in the imaging system. The imager 30 is further programmed to automatically determine respective offsets of its local clock relative to the reference clock for each time stamp associated with the acquired frames of imaging data. The acquired frames and the time stamps and local offsets associated with the acquired frames are uploaded to the DICOM server 38 via the DICOM image network 24. This data is transmitted in the format of DICOM objects, each DICOM object encapsulating a respective frame of imaging data and having a header comprising respective fields for a time stamp and an offset associated with that frame.

During the same study, physiologic data is acquired from the patient using the hemodynamic monitoring system 40. The hemodynamic monitoring system is programmed to automatically time stamp data in the acquired physiologic data representing one or more predetermined cardiac events with respective times generated by the local clock that dictates the time of day in the hemodynamic monitoring system. The hemodynamic monitoring system is further programmed to automatically determine respective offsets of its local clock relative to the reference clock for each time stamp associated with the physiologic data. The acquired physiologic data and the time stamps and the local offsets associated with the acquired physiologic data are uploaded to the DICOM server 38 via the DICOM waveform network 22. This data is transmitted in the format of DICOM objects, each DICOM object encapsulating respective physiologic data and having a header comprising respective fields for a time stamp and an offset associated with that physiologic data.

As previously described, the DICOM server 38 is programmed with a database management software module, by means of which the DICOM server 38 stores the imaging and physiologic DICOM objects in a database (not shown in FIG. 2B). This database management software also enables the DICOM server 38 to respond to requests for files from remote workstations. In particular, the DICOM server 38 can send the set of DICOM files for a study to a physician review station where quantitative imaging analysis can be performed. The quantitative analysis software module can be resident, for example, on the x-ray control station 52 (see FIG. 2A), the hemodynamic control station 50 (see FIG. 2B) or the physician review station 14 (see FIG. 1). The quantitative analysis software module will interpret the time stamps and local offsets in the DICOM objects for a study via the DICOM headers and merge the images with the physiologic data (e.g., ECG waveforms) for automatic image selection. In one embodiment of the quantitative analysis software module, when the physician replays the images, all the diastole frames and matching systole frames will be displayed. These displayed frames are selectable, for example, for left ventricular analysis. Individual frames for stenosis evaluation would be identified as to their contractility in the DICOM header. The quantitative analysis software would allow the physician to select an individual frame for quantitative coronary analysis (QCA) with an indicator to tell him/her whether it is at the peak or not when he/she selects a QCA tool. The physician could then frame forward or backward until the physician attains both the position and contractility he/she requires.

In accordance with one embodiment of the invention, the review station is a cardiology analysis system comprising an operator interface, a display monitor and a computer programmed to compensate for a lack of synchronism between the locals clocks of the imager 30 and the hemodynamic monitoring system 40. The lack of synchronism is compensated for by factoring in the associated local offsets when time stamps of frames of imaging data are compared to time stamps of physiological data corresponding to cardiac events of interest. In other words, the time stamps must be adjusted by the amount of offset before they are compared in order to obtain the true times of data acquisition relative to the reference clock. This enables the quantitative imaging analysis software module to automatically select a frame that was acquired in substantial synchronism with the occurrence of a predetermined cardiac event recorded in the physiological data for the study in issue. Quantitative coronary analysis is then performed based at least in part on the selected frame of imaging data. In the case of left ventricular analysis, for example, two frames corresponding to the diastole and systole of a particular cardiac cycle are selected and then analyzed.

In accordance with an alternative embodiment of the invention, the local clocks at the imager and hemodynamic monitoring system can be adjusted in real-time using the NTP time synchronization protocol to be synchronized with the reference clock. In this embodiment, the time stamps will represent adjusted, i.e., synchronized, time. Thus the header of each DICOM object will have a field containing the adjusted time stamp, but does not need a field for the local offset used to adjust the local clock.

The invention is not limited to use of NTP. Other distributed network time protocols that can be used include, for example, the Simple Network Time Protocol ("SNTP"), the Experimental Network Time Protocol ("XNTP"), the Secure Network Time Protocol ("STIME"), and the RealTime Transport Protocol ("RTP").

Figure 3:
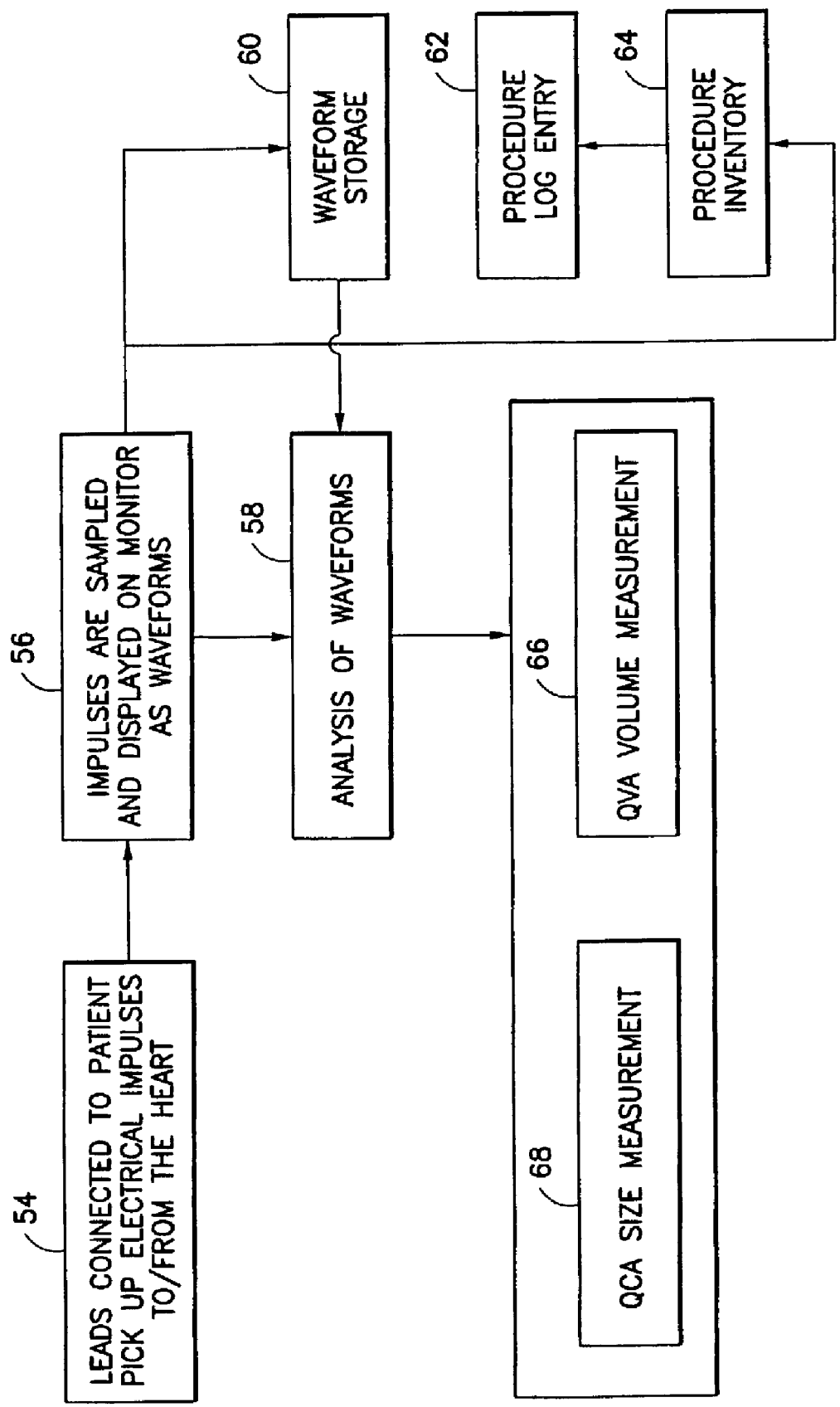
FIG. 3 is a flowchart indicating data acquisition by the hemodynamic monitoring system depicted in FIG. 2.

FIG. 3 is a flowchart showing various steps of the physiological monitoring process performed in the catheterization laboratory. The leads connected to the patient undergoing the procedure pick up electrical pulses to and from the patient's heart (step 54). The waveforms are stored in computer memory (step 60). The hemodynamic monitoring system is programmed to automatically perform ECG analysis of the waveforms (step 58), the results of which are also stored in computer memory. As part of that analysis, pointers to various characteristic features in the acquired waveforms are automatically time stamped. Optionally, quantitative analysis (QVA volume measurement 66 or QCA size measurement 68) can be performed at the hemodynamic control station. QCA and QVA software modules are not necessarily part of the hemodynamic monitoring system, but may reside on a PC connected to the latter. As previously described, while the procedure is under way, the hemodynamic technician will enter identifying codes and activate time stamps for the various procedures being performed (step 62). These procedures are maintained in a procedure log 64 called the "cath lab event log".

Figure 4:
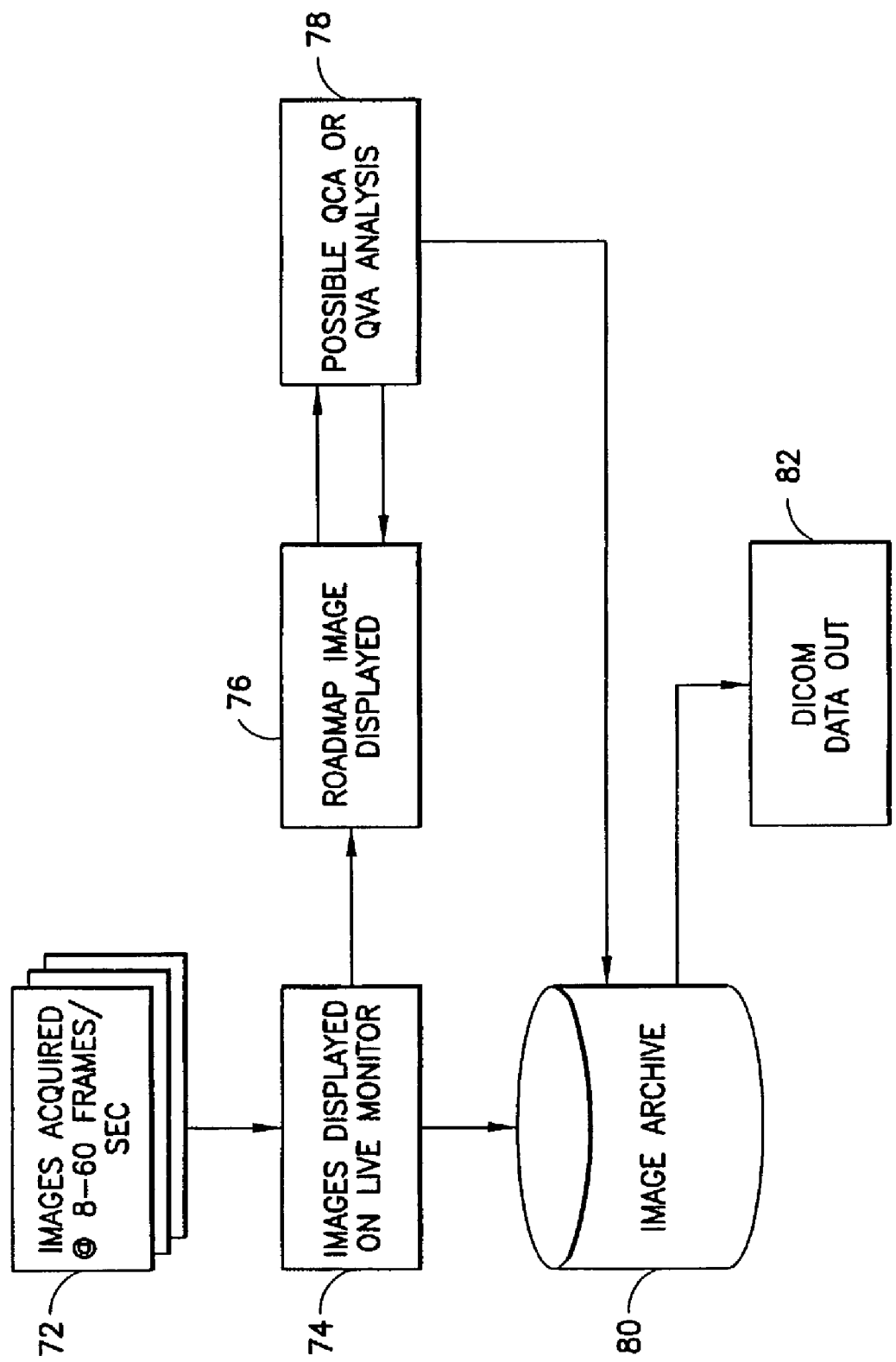
FIG. 4 is a flowchart indicating data acquisition by the x-ray imaging system depicted in FIG. 2.

FIG. 4 is a flowchart showing various steps of the imaging process performed in the catheterization laboratory. The x-ray images are typically acquired at a frame rate of 8 to 60 frames per second (step 72). The acquired images are displayed as live video (step 74) on the live video monitor (32 in FIG. 2A). A contrast-enhanced roadmap image is displayed (step 76) on the roadmap monitor (34 in FIG. 2A). The roadmap image assists the physician during guidance of the catheter through the patient's blood vessels and can also be used to perform quantitative image analysis (e.g., QCA or QVA) (step 78). The images are time stamped and stored in an image archive 80, along with the results of any quantitative image analysis. The image archive contains the database that is managed by the previously described DICOM server (38 in FIG. 2B). The DICOM server also downloads the DICOM data from the image archive 80 to a requesting workstation (step 82), e.g., via a TCP/IP network. The images can then undergo quantitative image analysis as previously described.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

The invention claimed is:

1. A method comprising the following steps:
    (a) acquiring frames of imaging data representing a succession of images of a patient's heart during a study using an imaging system;
    (b) automatically time stamping each acquired frame with respective times generated by a first clock;
    (c) automatically calculating respective offsets of said first clock relative to a reference clock for each time stamp associated with said acquired frames;
    (d) storing said acquired frames and said time stamps and said offsets associated with said acquired frames;
    (e) acquiring physiologic data from said patient during said study using a hemodynamic monitoring system;
    (f) automatically time stamping data in said acquired physiologic data representing one or more predetermined cardiac events with respective times generated by a second clock;
    (g) automatically calculating respective offsets of said second clock relative to said reference clock for each time stamp associated with said physiologic data;
    (h) storing said acquired physiologic data and said time stamps and said offsets associated with said acquired physiologic data;
    (i) computing which one of said acquired frames was acquired in substantial synchronism with a first predetermined cardiac event based on said time stamps and said offsets; and
    (j) associating a first acquired frame identified by step (i) with said first predetermined cardiac event,
    further comprising the step of displaying said first acquired frame of imaging data concurrently with acquired physiologic data having a visual indicator indicating a physiologic datum corresponding to said first predetermined cardiac event.

2. A method comprising the following steps:
    (a) acquiring frames of imaging data representing a succession of images of a patient's heart during a study using an imaging system;
    (b) automatically time stamping each acquired frame with respective times generated by a first clock;
    (c) automatically calculating respective offsets of said first clock relative to a reference clock for each time stamp associated with said acquired frames;
    (d) storing said acquired frames and said time stamps and said offsets associated with said acquired frames;
    (e) acquiring physiologic data from said patient during said study using a hemodynamic monitoring system;
    (f) automatically time stamping data in said acquired physiologic data representing one or more predetermined cardiac events with respective times generated by a second clock;
    (g) automatically calculating respective offsets of said second clock relative to said reference clock for each time stamp associated with said physiologic data;
    (h) storing said acquired physiologic data and said time stamps and said offsets associated with said acquired physiologic data;
    (i) computing which one of said acquired frames was acquired in substantial synchronism with a first predetermined cardiac event based on said time stamps and said offsets; and
    (j) associating a first acquired frame identified by step (i) with said first predetermined cardiac event; and
    (k) performing quantitative coronary analysis based at least in part on said first acquired frame.

3. The method as recited in claim 2, further comprising the steps of:
    (l) computing which one of said acquired frames was acquired in substantial synchronism with a second predetermined cardiac event based on said time stamps and said offsets; and
    (m) associating a second acquired frame identified by step (k) with said second predetermined cardiac event,
    wherein step (k) comprises performing left ventricular analysis based at least in part on said first and second acquired frames.

4. The method as recited in claim 3, wherein said first and second predetermined cardiac events are the diastole and systole of the same cardiac cycle.

5. The method as recited in claim 2, further comprising the steps of automatically performing ECG analysis on said acquired physiologic data to identify said acquired physiologic data representing said predetermined cardiac events.

6. The method as recited in claim 2, wherein step (g) is performed using a distributed network clock synchronization protocol.

7. The method as recited in claim 2, wherein said acquired frames of imaging data and said acquired physiologic data are stored in an asynchronous server.

8. The method as recited in claim 2, wherein each of said acquired frames of imaging data is encapsulated in a DICOM object having a header containing respective fields for an associated time stamp and an associated offset.

9. The method as recited in claim 2, wherein said imaging data is acquired using X-rays.

10. The method as recited in claim 2, further comprising the step of injecting a contrast agent into the cardiovascular system of said patient before said frames of imaging data are acquired.

11. The method as recited in claim 2, wherein said physiologic data comprises electrocardiogram waveform data.

12. The method as recited in claim 2, wherein said physiologic data comprises blood pressure measurement data.

13. The method as recited in claim 2, wherein one of said predetermined cardiac events is the onset of cardiac contraction.

14. The method as recited in claim 2, wherein one of said predetermined cardiac events is peak cardiac contraction.

15. A method comprising the following steps:
(a) automatically determining a first offset of a first local clock relative to a reference clock, said first local clock dictating the time of day in an imaging system;
(b) automatically adjusting said first local clock by an amount that is a function of said first offset to synchronize said first local clock with said reference clock;
(c) automatically determining a second offset of a second local clock relative to said reference clock, said second local clock dictating the time of day in an hemodynamic monitoring system;
(d) automatically adjusting said second local clock by an amount that is a function of said second offset to synchronize said second local clock with said reference clock;
(e) acquiring a frame of imaging data representing an image of a patient's heart during a study using said imaging system;
(f) automatically time stamping said acquired frame with a time generated by said adjusted first local clock;
(g) storing said acquired frame and said time stamp associated with said acquired frame as an imaging file;
(h) acquiring physiologic data from said patient during said study using said hemodynamic monitoring system;
(i) automatically time stamping a datum in said acquired physiologic data representing a predetermined cardiac event with a time generated by said adjusted second local clock; and
(j) storing said acquired physiologic data and said time stamp associated with said acquired physiologic data as a physiology file,
wherein steps (a) through (j) are performed repeatedly over the course of a study to acquire a multiplicity of frames of imaging data and physiologic data, further comprising the steps of:
selecting a frame of imaging data acquired by said imaging system at a time substantially synchronized with a predetermined cardiac event recorded in said physiologic data acquired by said hemodynamic monitoring system, said frame selection being based on comparison of time stamps in imaging files with time stamps in physiology files, said selected frame having a time stamp that differs from a time stamp associated with a physiologic datum corresponding to said predetermined cardiac event by a minimum amount; and
performing quantitative analysis based at least in part on said selected frame of imaging data.

16. The method as recited in claim 1, wherein step (g) is performed using a distributed network clock synchronization protocol.

17. The method as recited in claim 1, wherein said acquired frames of imaging data and said acquired physiologic data are stored in an asynchronous server.

18. The method as recited in claim 1, wherein each of said acquired frames of imaging data is encapsulated in a DICOM object having a header containing respective fields for an associated time stamp and an associated offset.

19. The method as recited in claim 1, wherein said imaging data is acquired using X-rays.

20. The method as recited in claim 1, further comprising the step of injecting a contrast agent into the cardiovascular system of said patient before said frames of imaging data are acquired.

21. The method as recited in claim 1, wherein said physiologic data comprises electrocardiogram waveform data.

22. The method as recited in claim 1, wherein said physiologic data comprises blood pressure measurement data.

* * * * *